(12) United States Patent
Montrose

(10) Patent No.: US 8,613,732 B2
(45) Date of Patent: Dec. 24, 2013

(54) SKIN THERAPY SYSTEMS

(75) Inventor: Deanna Montrose, Phoenix, AZ (US)

(73) Assignees: Deanna Montrose, Phoenix, AZ (US); Paraffin internatinal, LLC, Phoenix, AZ (US)

( * ) Notice: Subject to any disclaimer, the term of this patent is extended or adjusted under 35 U.S.C. 154(b) by 0 days.

(21) Appl. No.: 13/560,487

(22) Filed: Jul. 27, 2012

(65) Prior Publication Data

US 2013/0096515 A1   Apr. 18, 2013

Related U.S. Application Data

(60) Provisional application No. 61/589,752, filed on Jan. 23, 2012, provisional application No. 61/548,173, filed on Oct. 17, 2011.

(51) Int. Cl.
*A61M 35/00* (2006.01)

(52) U.S. Cl.
USPC .......................................... 604/292; 604/290

(58) Field of Classification Search
USPC ................................. 604/290–293
See application file for complete search history.

(56) References Cited

U.S. PATENT DOCUMENTS

| | | | | |
|---|---|---|---|---|
| 2,210,618 A | * | 8/1940 | De St Cyr | 604/292 |
| 4,622,035 A | * | 11/1986 | Palmer et al. | 604/293 |
| 5,520,940 A | * | 5/1996 | Tirkkonen | 426/132 |
| 5,614,202 A | | 3/1997 | DeFina | |
| 6,174,319 B1 | * | 1/2001 | Desnos | 606/133 |
| 6,503,944 B1 | | 1/2003 | Chanchani | |
| 6,673,054 B1 | * | 1/2004 | Gould et al. | 604/292 |
| 6,749,860 B2 | * | 6/2004 | Tyrrell et al. | 424/404 |
| 7,658,942 B2 | | 2/2010 | Deckner | |
| 2009/0227967 A1 | | 9/2009 | Donovan | |
| 2010/0065081 A1 | | 3/2010 | Vracknos | |
| 2011/0190714 A1 | * | 8/2011 | Oda et al. | 604/291 |

\* cited by examiner

*Primary Examiner* — Susan Su
(74) *Attorney, Agent, or Firm* — Yu Cai; Polsinelli PC

(57) ABSTRACT

A convenient and hygienic skin therapy system comprising an encaser, one or more therapeutic compositions, a sealing means and optional accessories is disclosed. A method of using such a skin therapy system is also provided. The skin therapy system and the use thereof provides an effective, efficient and safe therapeutic approach.

20 Claims, 10 Drawing Sheets

SKIN THERAPY SYSTEMS

CROSS REFERENCE TO RELATED APPLICATIONS

This application claims the priority to U.S. provisional application entitled WAX THERAPY SYSTEMS, assigned application No. 61/589,752, filed on Jan. 23, 2012 and U.S. provisional application entitled PARAFFIN THERAPY SYSTEMS, assigned application No. 61/548,173, filed on Oct. 17, 2011, which are hereby incorporated by reference in their entirety.

FIELD OF THE INVENTION

This invention relates to providing a system for improved skin therapies. More particularly, this invention relates to providing a convenient and hygienic system of single-use therapy devices containing various therapeutic compositions for skin treatment.

BACKGROUND OF THE INVENTION

Wax-based or liquid-based therapeutic compositions applied externally to the skin may be used as a means for conditioning skin, softening skin and relieving joint pain, among other uses. In such a treatment, the wax-based or liquid-based therapeutic compositions are often heated to a melting state or to a certain temperature and the body portion targeted for treatment, such as hands or feet, are brought into contact with the therapeutic composition. Current methods of melting bulk quantities of wax-based or liquid-based therapeutic compositions for dipping of hands or feet takes time (typically two-three hours), which is inconvenient for a commercial entity providing such therapy services. Further, repeated heating-cooling cycles of bulk wax-based or liquid-based therapeutic compositions for skin therapy reduces the effectiveness of the composition over time, creates a risk of biological cross-contamination, and poses potential health risks for the subjects under the therapy. Therefore, a need exists for improved methods and apparatuses associated with this type of therapy which provides fast, contamination-free, portable, user-friendly means for application of various skin therapeutic compositions.

BRIEF SUMMARY OF THE INVENTION

Provided herein is a skin therapy system for skin conditioning or treatment of a body part. The system comprises: a) a body part shaped encaser configured to fit for a body part targeted for skin treatment; b) one or more predetermined amounts of therapeutic compositions enclosed in the body part shaped encaser, wherein the therapeutic composition comprises about 25 wt % to about 75 wt % paraffin and about 25 wt % to about 75 wt % coconut oil, by weight of the composition; and (c) a sealing means that seals the body part shaped encaser enclosing the one or more therapeutic compositions, wherein the sealing means is attached to the body part shaped encaser or is detached from the body part shaped encaser. In some embodiments, the skin therapy system of claim 1, further comprises one or more accessories selected from the group consisting of encaser liner, temperature indicator, attach means, external padding, outer pouch, coverlet, harness, heating or temperature maintaining element, and any combination thereof. In some embodiments, the body part shaped encaser is configured in a form selected from the group consisting of a glove, a mitten, a muff, a fingerstall, a sock, a slipper, a shoe, a booty, a bonnet, a skullcap, a facial mask, and any other structure adaptable for covering an area of skin of a body part to be treated. The body part shaped encaser may be made from material selected from the group consisting of carbon-fiber, polyethylene, metal foil, and any combination thereof. The body part shaped encaser may be made in a standard size and dimension. In some embodiments, the body part shaped encaser further comprises an encaser liner of similar size, dimension and shape to the encaser, and wherein the encaser liner is inserted in the body part shaped encaser and the one or more therapeutic compositions is enclosed in the encaser liner. Generally, the encaser liner is made from material selected from the group consisting of paper, textile, non-woven fabrics, plastic fabrics, non-woven polypropylene fabrics, and any combination thereof.

The one or more therapeutic compositions of the skin therapy system comprising about 25 wt % to about 75 wt % paraffin and of about 25 wt % to about 75 wt % coconut oil may further comprises one or more additional ingredient selected from essential oils, anti-oxidants, fragrances, colors, emollients and any combination thereof. In some embodiments, the one or more therapeutic compositions further comprise about 2 wt % to 7 wt %, by weight of the composition, of a mixture of antioxidants comprising tocopheryl acetate. In some embodiments, the mixture of antioxidants further comprises one or more additional ingredient selected from the group consisting of sunflower seed oil, safflower oil, rice bran oil, almond oil, apricot oil, wheat germ oil, lecithin, and any combination thereof. Further, the paraffin in the therapeutic composition is selected from the group consisting of paraffin wax, liquid paraffin oil and petroleum jelly. In some embodiments, the one or more therapeutic compositions enclosed in the body part shaped encaser liquefies in between about 1 and about 5 minutes at a temperature ranging between about 113° F. to about 131° F.

In one embodiment, the sealing means of the skin therapy system is a vacuum seal to keep air out of the body part shaped encaser enclosing the one or more therapeutic compositions.

In some embodiments, the skin therapy system further comprises one or more temperature indicators, wherein the temperature indicator is attached to an exterior surface of the body shaped encaser. The temperature indicator may be a thermochromatic indicator in a form selected from the group consisting of a coating, a strip, a sticker, a label, a patch, a tape, and any other available form.

Also provided herein is a method of using a skin therapy system for skin conditioning or treatment of a body part, and the method comprises the steps of (a) pre-heating a body part shaped encaser of the skin therapy system to liquefy one or more therapeutic compositions therapeutic compositions enclosed in the body part shaped encaser at a temperature ranging between about 113° F. to about 131° F., wherein the therapeutic composition comprises between about 25 wt % to about 75 wt % paraffin and between about 25 wt % to about 75 wt % coconut oil, by weight of the composition; (b) removing a sealing means of the body part shaped encaser enclosing the therapeutic composition; (c) inserting a body part targeted for skin treatment into the encaser to put the skin in direct contact with the therapeutic composition; (d) attaching the body part shaped encaser enclosing the therapeutic composition to the body part using an attachment means; and (e) detaching the body part shaped encaser enclosing the therapeutic composition from the body part after a predetermined amount of time.

Other aspects and iterations of the invention are described in more detail below.

DETAILED DESCRIPTION OF THE INVENTION

Figure 1:
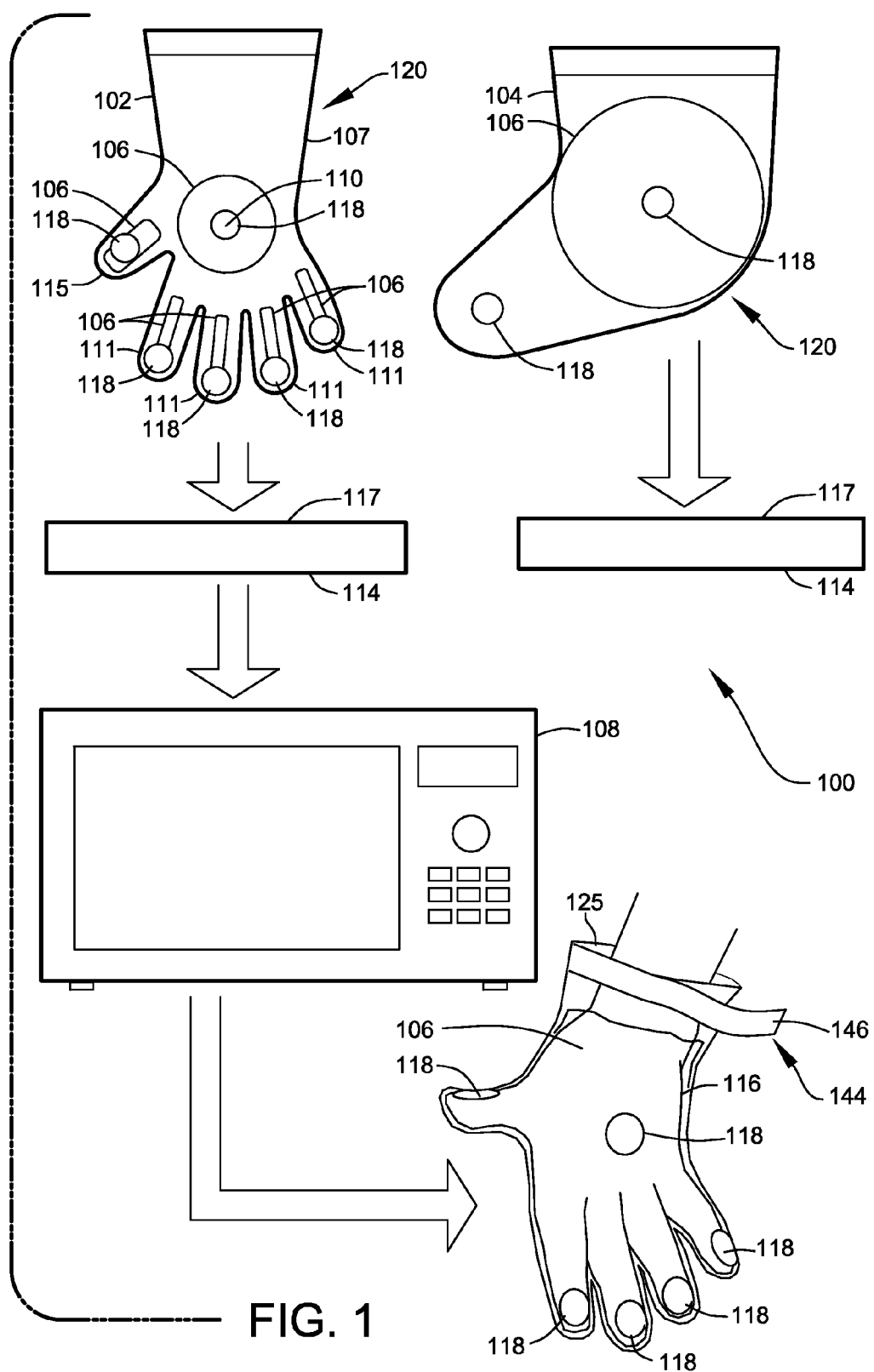
FIG. 1 shows a schematic diagram illustrating single-use paraffin-based therapy devices of the wax therapy systems, according to a preferred embodiment of the present invention.

The skin therapy device as provided herein allows for a shortened time in preparing or maintaining a therapeutic composition while heating, cooling, spreading, temperature maintaining, and/or solidifying without causing cross-contamination and simplifies the process of skin application prior to, during and after the therapy, when compared with conventional treatment process. Also provided is the method for using the skin therapy system disclosed herein for skin treatment purposes.

I. The Skin Therapy System

The present invention relates to a skin therapy system comprising: (1) an encaser, (2) a predetermined amount of therapeutic composition enclosed in the encaser, and (3) a sealing means to seal the encaser. The skin therapy system may further comprise one or more additional accessories selected from encaser liner, thermochromatic indicators, attaching means, and heating elements, among other components. The encaser may be made of various materials, in a predetermined shape, and with various dimensions. The therapeutic composition may be solid, semi-solid or liquid-based. In addition, the sealing means of the encaser allows the containment and enclosure of the therapeutic composition to be with air or air-free prior to use.

1. Encaser

The device is designed for single-use applications, and it comprises at least one body-appendage encaser structured and arranged to encase at least one body appendage of a human body. The encaser may be made of carbon-fiber, plastic, transparent/translucent polymer such as polyethylene, metal foil, depending on design requirements and heating sources. The encaser may be made of elastic material that allows for expanding or stretching. The material used to make the encaser is heat-durable, and does not release toxic chemicals upon heating. The encaser of the device may be in any shape that is desirable and adaptable for covering an area of skin to be treated, and thus it may be in the shape of a hand, a foot or any kind of body part such that the encaser is configured in the form of a glove, a mitten, a muff, a fingerstall, a sock, a slipper, a shoe, a booty, a bonnet, a skullcap, or a mask in the form of all or part of the face, or any other applicable forms and shapes. In one embodiment, the encaser is hand shaped. In another embodiment, the encaser is foot shaped. In one embodiment, the body part shaped encaser may be unisized, such that it references to the average body part size acceptable in the industry. In one embodiment, the encaser may be unisized for women's hands or feet. In one embodiment, the encaser may be unisized for men's hands or feet. In one embodiment, the encaser may be stretchable such that it can fit for any size of body part of a man and/or a woman. The encaser may also be manufactured in a series of sizes that are standard in the industry, such like the standard sizes for gloves, shoes, and other similar products. The encaser may have in-folds, which provide a three-dimensional shape that better accommodates the shape and dimension of a body part upon usage. In one embodiment, the encaser is foot-shaped, with an in-fold providing a sole of a slipper, a boot, a shoe upon expanding.

FIG. 1 shows a schematic diagram depicting one or more embodiments of a single-use body part-shaped encaser 120 to exemplify the skin therapy systems 100. Single-use body part-shaped therapy device 120 utilizes at least one single-use glove 102 or, alternately, at least one single-use boot 104. Such a single-use glove 102 or single-use boot 104 comprises a hand or foot encaser means for encasing at least one human hand or foot. Preferably, each single-use glove 102 or each single-use boot 104, contains at least one therapeutic composition 106, which preferably may be quickly heated (preferably from about one to about four minutes) by various heating sources including, but not limited to, a microwave oven 108.

In one embodiment, each single-use glove 102 or single-use boot 104 preferably is structured and arranged to be a sanitary one-time-use disposable product as further described herein. Upon reading this specification those of ordinary skill in the art will appreciate that, under appropriate circumstances, other device configurations, such as, for example, arm wraps, leg wraps, etc., may suffice. Preferred embodiments of skin therapy system 100, as described herein, preferably function to warm the skin to help soften dead skin (thus facilitating exfoliation). In addition, preferred embodiments of skin therapy system 100 preferably function to warm joints and assist with circulation.

Figure 2:
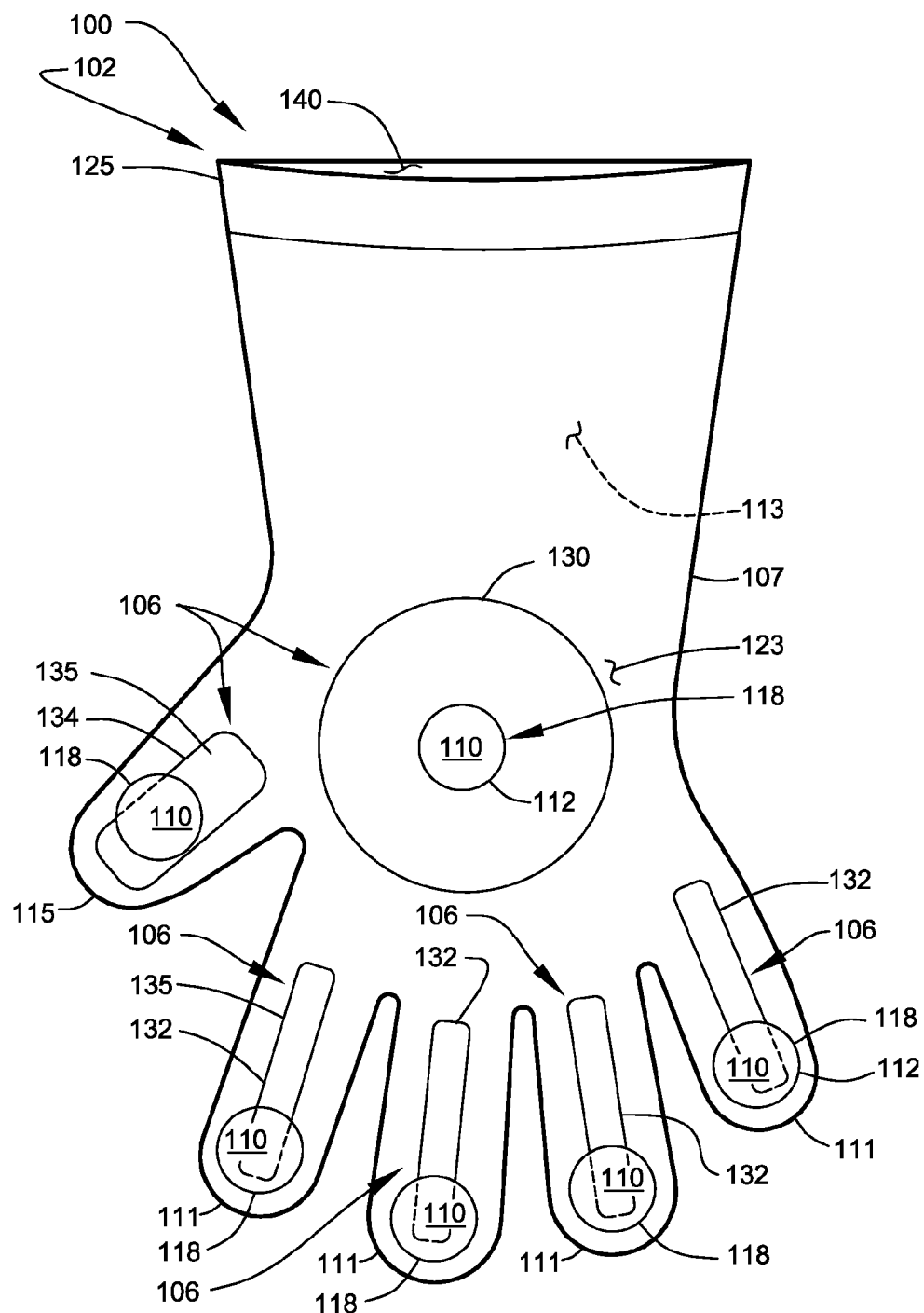
FIG. 2 shows a top view illustrating a hand glove of the wax therapy systems, according to a preferred embodiment of FIG. 1.

As one example, FIG. 2 shows a top view, illustrating a single-use glove 102 of the skin therapy system 100. Single-use glove 102 preferably comprises therapeutic composition 106 positioned in each finger portion 111 and thumb portion 115 and at the palm position 123, as shown. In one embodiment, the palm region 123 of single use glove 102 comprises at least one first quantity of therapeutic composition 106. As shown in FIG. 2, the therapeutic composition 106 is placed within the interior of the single-use glove 102 in the palm region 123. In another embodiment, each single-use glove 102 comprises at least one second quantity of therapeutic composition 106 placed within the interior of the glove in each of the finger portions 111 and thumb portion 115, as shown. The therapeutic composition 106 in the palm region and the hand digit portions 111 and 115 may be the same or different.

As shown in FIG. 2, single-use glove 102 comprises one substantially flexible containment wall 107 having an interior portion 113 structured and arranged to contain at least one palm composition 130, a finger composition 132, and a thumb composition 134. Containment wall 107 further comprises an access opening, which is a hand aperture 140 in the single-use glove 102 embodiment. Hand aperture 140 preferably permits a user to insert a hand into the single-use glove 102, during use. Hand aperture 140 preferably comprises a width, when flat, of about seven inches. Single-use glove 102 may further comprise at least one thermochromatic indicator 118, optionally positioned at any finger-tip, at the thumb-tip, at the palm area, or anywhere the thermochromatic indicator may sense the temperature of the therapeutic composition enclosed in the single-use glove 102.

Figure 3:
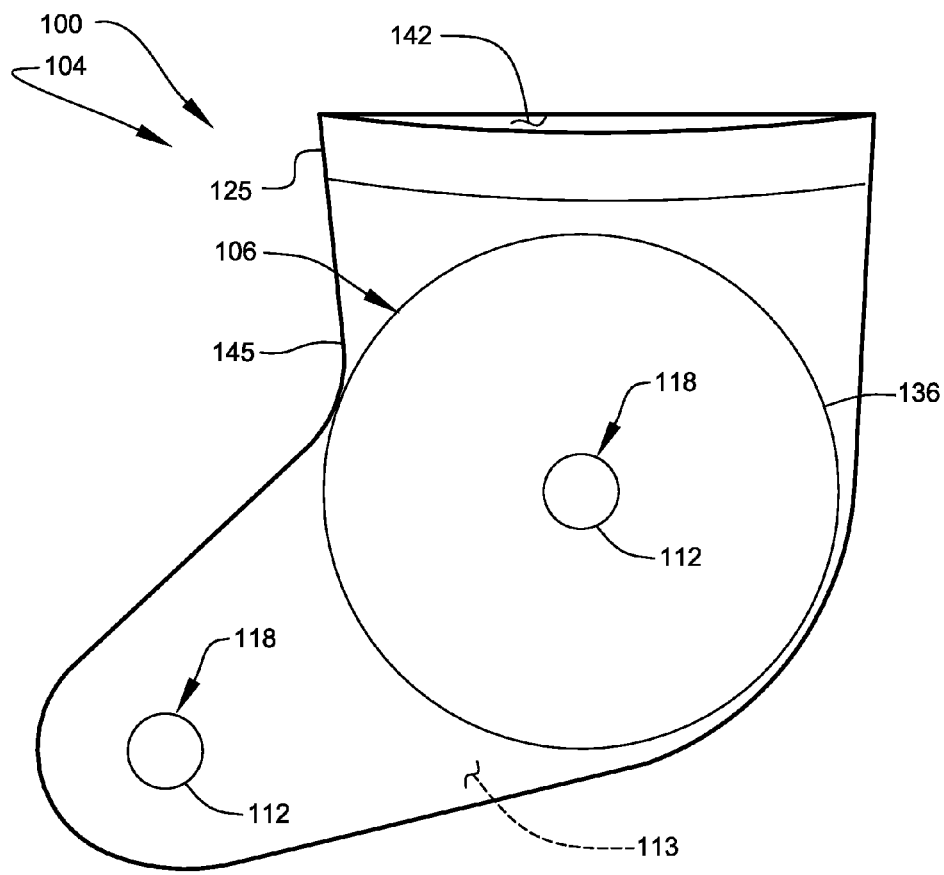
FIG. 3 shows a top view illustrating a foot boot of the wax therapy systems, according to the preferred embodiment of FIG. 1.

FIG. 3 shows a top view illustrating a single-use boot 104 of the skin therapy system 100. In one embodiment, the single-use boot 104 comprises a therapeutic composition 106 positioned in the ankle region 145, and/or toe region, of the single-use boot 104. Therapeutic composition 106 in ankle region 145 of single-use boot 104 preferably comprises at least one ankle composition 136. In addition, the single-use boot 104 comprises at least one foot aperture 142. Preferably foot aperture 142 permits the user to insert a foot into the single-use boot 104, during use. Foot aperture 142 preferably comprises a width, when flat, of about ten inches.

Figure 11A:
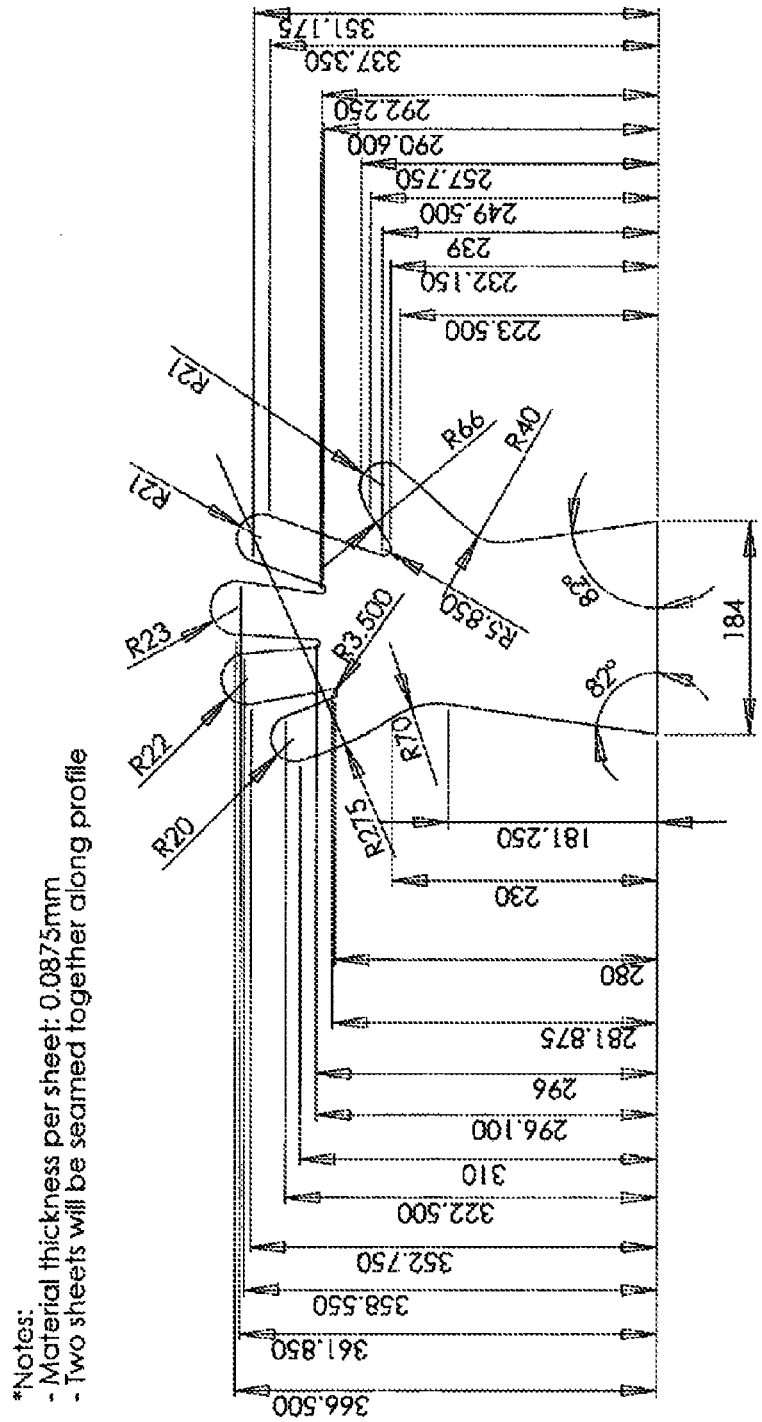
FIG. 11 shows additional dimensions and details of (A) a glove and (B) a boot, exemplifying the single use body part shaped encaser of the wax therapy systems.
Figure 11B:
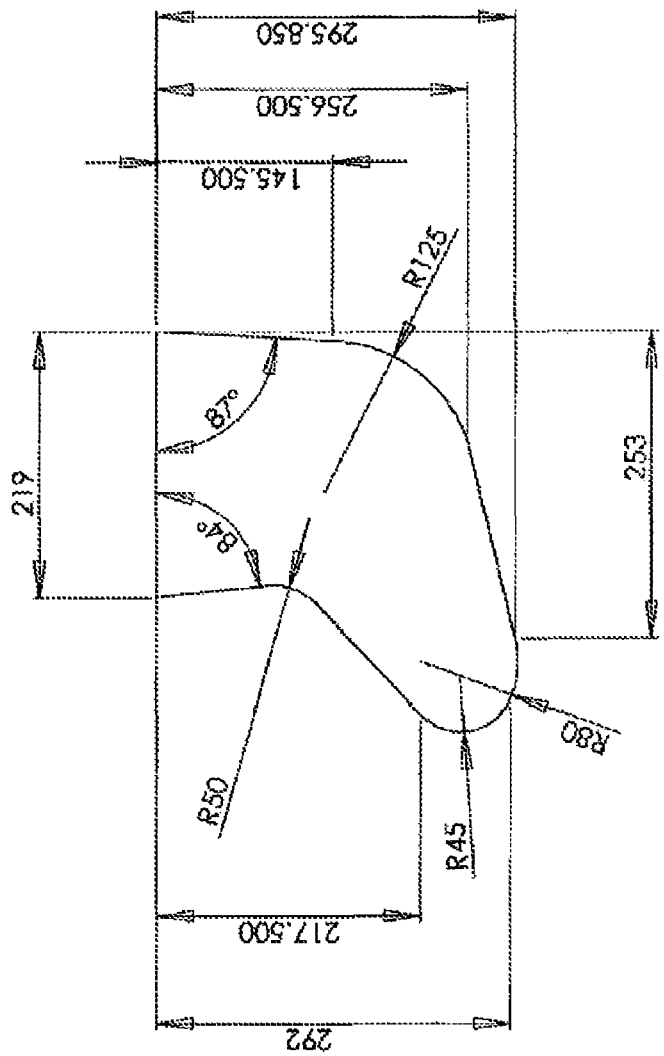

FIGS. 11A and 11B depict exemplary dimensions and details of an embodiment of a single-use glove 102 and single-use boot 104 for the skin therapy system 100. Upon reading this specification, those with ordinary skill in the art will now appreciate that, under appropriate circumstances, considering such issues as design preference, user preferences, marketing preferences, cost, structural requirements, available materials, technological advances, etc., other glove and boot material arrangements that meet or exceed criteria set forth herein may suffice. In addition to customized manufacturing a single-use glove 102 and single-use boot 104 encaser, boot 104 (without any therapeutic composition) is also commercially available for purchase, for example, the Sani-boot made by Keystone, or similar products through Pro-safety of Milwaukee Wis.

2. Therapeutic Compositions

The therapeutic compositions applicable for the skin therapy system 100 may be wax-based, liquid-based, or gel-based; all of which are to be spread evenly inside the encaser in a pre-determined amount prior to skin application. For a wax-based composition, the solidified composition is spread into a thin layer in a body part shaped encaser with the shape essentially the same as the encaser. For a liquid based composition, a predetermined amount of the composition sufficient to cover targeted skin area is enclosed in a body part shaped encaser. The therapeutic composition is contained inside the encaser without the risk of leaking, spill, evaporation, or cross-contamination, and can readily be applied to the skin area without the need of further spreading while providing nearly even and direct contact to skin under treatment.

The therapeutic compositions applicable for the skin therapy system may 100 comprise various ingredients, which are selected according to their physical, chemical, or pharmaceutical characteristics suitable for the skin therapy system 100 and therapeutic targets. The wax-based, liquid-based, or gel-based therapeutic composition is pre-packaged into the encaser of the skin therapy system 100 and may or may not require heating prior to skin application. In other embodiments, the wax-based, liquid-based, or gel-based therapeutic composition may be installed into the encaser customarily prior to a therapy session. The Section II below provides further details of therapeutic compositions.

Each encaser of the skin therapy system 100 may comprise one or more therapeutic compositions 106. In one embodiment, one or more therapeutic compositions 106 is positioned in a single-use body part shaped encaser at time of manufacturing. In one embodiment, a single therapeutic composition 106 is uniformly positioned in a single-use body part shaped encaser, such that the therapeutic composition 106 is spread about evenly as a thin layer throughout the encaser. In one embodiment, the therapeutic composition 106 in a body part shaped encaser is a contiguous thin layer of solidified or gel like form extending evenly to each portion or region of an encaser until the lower end of containment wall away from aperture. Depending on the therapeutic composition (solid or gel, wax-, mud- or clay-based mixture), the thickness of the contiguous thin layer of the composition may be between about 0.1 inch to about 1.5 inches. In one embodiment, a solid form therapeutic composition 106 of a quantity may be molded into a certain shape of certain size before positioned in a body part shaped encaser. In another embodiment, a therapeutic composition 106 of a quantity may be added in to a body part shaped encaser when the composition is in a liquefied state, which then it's solidify or gelification with or without assisted pressing molds the composition into the shape of the encaser upon cooling or sitting. Upon reading this specification, those with ordinary skill in the art will now appreciate that, under appropriate circumstances, considering such issues as design preference, user preferences, marketing preferences, cost, structural requirements, available materials, technological advances, etc., other therapeutic substance insert arrangements such as, for example, pre-coating of the internal glove, linked portions insertable into the glove, etc., may suffice.

In another embodiment, a quantity of a first therapeutic composition 106 is placed in each of the fingers and thumb portion of a hand shaped encase, and a quantity of a second therapeutic composition 106 is placed in the palm region of a single-use body part shaped encaser; wherein the first therapeutic composition 106 heats up at a slightly slower rate than the second therapeutic composition 106 placed in the palm region such that, upon heating, all of therapeutic composition 106 placed into a hand shaped encase will heat up or melt about equally and reach a predetermined temperature at about the same time. Even heating without overheating any portion of a therapeutic composition 106 is important for even liquefaction of solid form therapeutic composition, and the safe use of the skin therapy system 100 to prevent skin injure due to excessive or uneven heat during the direct skin-composition contact in a skin therapy.

As exemplified in FIG. 2, therapeutic composition 106 in each finger 111 preferably comprises at least one finger composition 132, or alternately, in thumb portion 115 at least one thumb composition 134. Finger composition 132 preferably comprises enough therapeutic composition 106, when melted or heated, to substantially coat each finger portion of single-use glove 102. In one embodiment, finger composition 132 comprises about one-half ounce of therapeutic composition 106. Thumb composition 134 preferably comprises enough therapeutic composition 106, when melted or heated, to substantially coat the thumb of single-use glove 102. In one embodiment, thumb composition 134 comprises about one ounce of therapeutic composition 106. In one embodiment, finger composition 132 and thumb composition 134 comprise at least one insert 135, which may be a bar as shown, or pellets, or a film of spread thin layer of solidified or gel like therapeutic composition 106. In one embodiment, finger composition 132 comprises an insert 135 as a bar having a length of about three inches, a width of about one-half inch, and a thickness of about one-half inch. In one embodiment, thumb composition 134 comprises an insert 135 as a bar having a length of about two-and one-half inches, a width of about one inch, and a thickness of about one-half inch.

Therapeutic composition 106 in the palm position 123 comprises at least one palm composition 130. Palm composition 130 preferably comprises enough therapeutic composition 106, when melted or heated, to substantially coat the palm area of single-use glove 102. In one embodiment, palm composition 130 comprises at least one insert of the therapeutic composition 106, which may be in a form of a circular disc, as shown, or a bar, or pellets, or a film of evenly spread out solidified or gel like thin layer. In one embodiment, palm composition 130 comprises two-and-one-quarter ounces of therapeutic composition 106. In one embodiment, palm composition 130 in a form of circular disk comprises a diameter of about four inches, and a thickness of about one-half inch.

As exemplified in FIG. 3, therapeutic composition 106 in ankle region 145 of single-use boot 104 preferably comprises at least one ankle composition 136. In one embodiment, ankle composition 136 comprises enough therapeutic composition 106, when melted, to substantially coat single-use boot 104. Ankle composition 136 preferably comprises about six ounces of therapeutic composition 106. In one embodiment, ankle composition 136 is in a form of at least one insert, which may be a circular disc, as shown, or a bar, or pellets, or a film of evenly spread out solidified or gel like thin layer. In one embodiment, ankle composition 136 in a form of circular disc comprises a diameter of about eight inches and a thickness of about one-quarter inch. In one embodiment, the therapeutic composition 106 is inserted as a contiguous thin layer of solidified or gel like form extending evenly to ankle region 145, each toes of the encaser until to the bottom of the tops 125 away from foot aperture 142.

3. Sealing Means

Hand aperture 140 or foot aperture 142 may be sealed or partially sealed to prevent spilling of therapeutic composition 106 outside of the body part shaped encaser 120 during heating and application. In one embodiment, the apertures 140 and 142 are sealed by folding, zip lock, removable tape or adhesive strips, removable adhesive, sewing, iron-on or heat seals, such that air or steam in the encaser may be released when the seal is removed and the encaser is heated. In one embodiment, the apertures 140 and 142 are partially sealed to permit venting of any accumulated gases associated with heating of therapeutic composition 106. Other venting arrangements such as, for example, one-way vents, slits, re-sealable portals, etc., may also be applicable. In one embodiment, the apertures 140 and 142 are vacuum sealed, such that the encaser stays air-free during heating, the heat and moist in the encaser are retained, and the explosion or expanding of the encaser during heating can be avoided. The sealing means of a body part shaped encaser may be removed by cutting, trimming, or tearing after heating and prior to skin application.

Figure 4A:
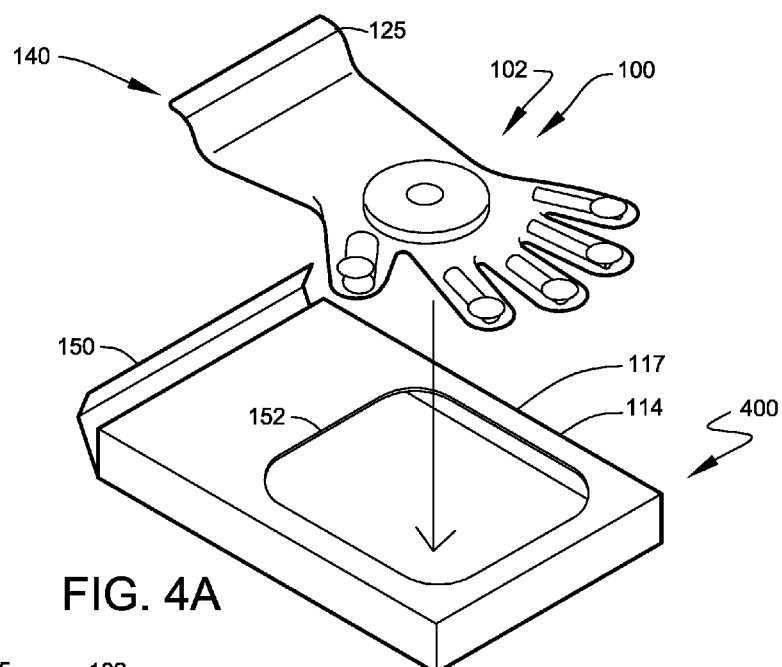
FIG. 4A shows a perspective view illustrating a preferred container for holding and heating of the single-use paraffin-based therapy device of the wax therapy systems, according to the preferred embodiment of FIG. 1.
Figure 4B:
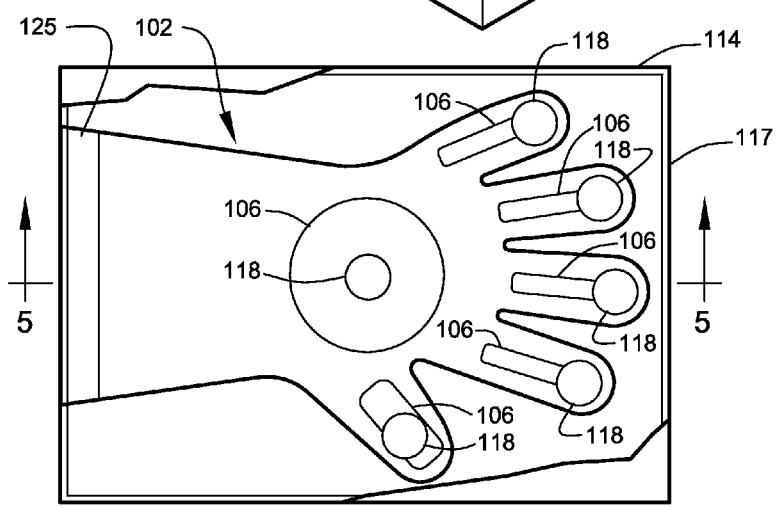
FIG. 4B shows a plan view in partial section illustrating the preferred container for holding and heating of the single-use paraffin-based therapy device of the wax therapy systems, according to the preferred embodiment of FIG. 4A.
Figure 5:
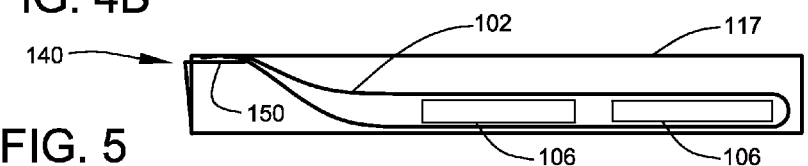
FIG. 5 shows a cross-sectional view along section 5-5 of FIG. 4B.
Figure 6A:
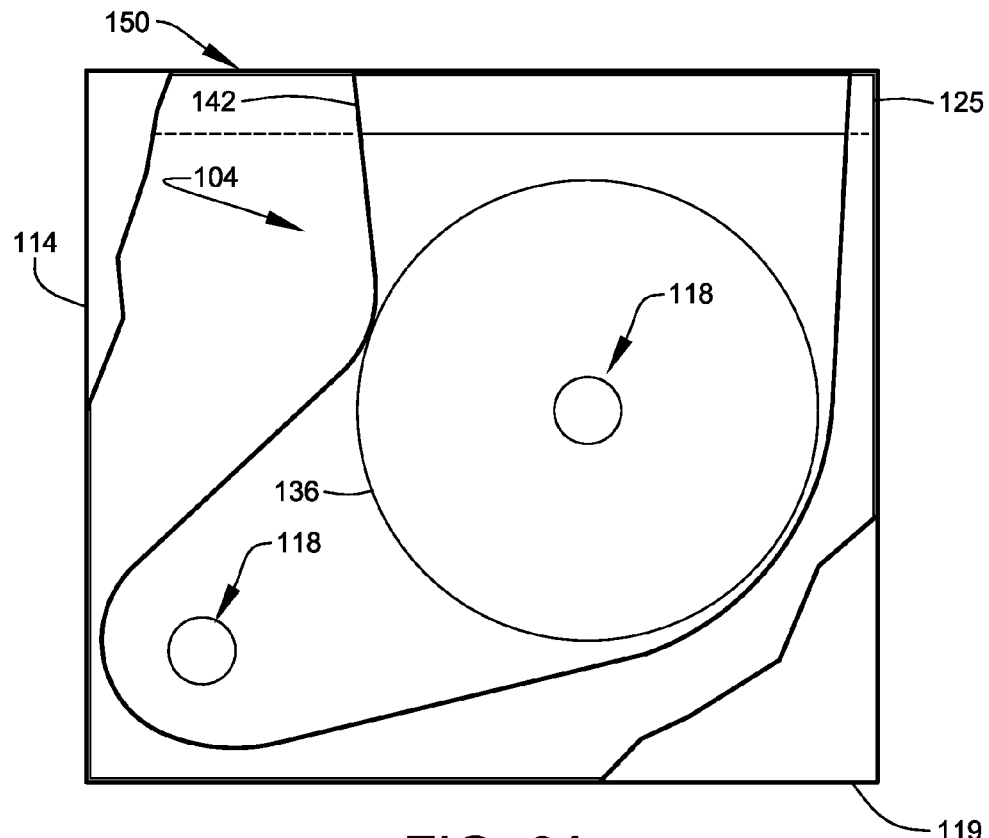
FIG. 6A shows a plan view in partial section illustrating an alternately preferred container for holding and heating of the single-use paraffin-based therapy device of the wax therapy systems, according to the preferred embodiment of FIG. 1.

In another embodiment, a closure 150, as best shown in FIG. 5, of a sealing box 114 may be used to hold and seal hand aperture 140 and foot aperture 142 (shown in FIG. 6A). The tops 125 of the gloves 102 and boots 104 preferably have an extended length along respective wrist (glove) and ankle (boot) portions as shown in FIG. 2 and FIG. 3. Once therapeutic composition 106 is positioned in single-use wax-based therapy device 120, each device preferably is folded over on the opened end (aperture) and placed in the sealing box 114, with the folded portion of the aperture aligned with the flap of the closure 150 of the sealing box 114 as shown in FIGS. 4A, 4B and 5. The flap of the closure 150 is elevated with respect to the rest of single-use body part shaped device 120 when the closure 150 is in a closed position as shown in FIG. 5. The elevated position of the hand aperture 140 or foot aperture 142 provided by the elevated flap closure 150 when the sealing box 114 is closed seals the aperture and prevents spilling of therapeutic composition 106 outside of single-use body part shaped device 120 during heating by further utilizing the gravity. Closure 150 also permits venting of any accumulated gases associated with heating of therapeutic composition 106.

FIG. 4A shows a perspective view illustrating a preferred container 117 for holding and heating of single-use hand shaped device 120 of skin therapy system 100. FIG. 4B shows a plain view of the container 117 holding a single-use hand shaped device 120 of skin therapy system 100, and FIG. 5 shows a side view through section 5-5 of FIG. 4B. In addition, FIG. 6A shows a plan view illustrating an alternately preferred container 119 for holding and heating of single-use foot-shaped device 120 of the skin therapy system 100.

The sealing box 114 may further comprise at least one window 152 in addition to at least one closure 150 (FIG. 4A). Window 152 permits viewing of thermal chromatic indicator 118 (described below Section 4(b)), during heating, to visually determine the proper temperature. Window 152 also permits viewing therapeutic composition 106, during heating, to visually determine complete melting of therapeutic composition 106. Upon reading this specification, those with ordinary skill in the art will now appreciate that, under appropriate circumstances, considering such issues as design preference, user preferences, marketing preferences, cost, structural requirements, available materials, technological advances, etc., other viewing arrangements such as, for example, multiple smaller portals, multiple windows, slits, pop-up notifiers, sound notifiers, etc., may suffice.

In one embodiment, one or more single-use therapy devices 120 is placed in one sealing box 114. In another embodiment, an individual single-use therapy device 120 is placed in one sealing box 114. The sealing box 114 may be for single-use or may be used repeatedly. In one embodiment, the external sealing box is microwavable. Microwavable sealing box 114 preferably comprises at least one microwave-safe material selected from cardboard, a wood-pulp material, carbon-fiber, microwavable plastics, ceramics, wood derivative materials, and any combination thereof.

4. Optional Accessories (a) Encaser Liner

Optionally, an encaser liner may be inserted into the encaser of the skin therapy device. In one embodiment, the encaser liner has the same shape and dimension as the encaser, with a size slightly smaller or substantially the same such that the encaser liner can be inserted into the encaser with ease. When the encaser is equipped with an encaser liner, the therapeutic composition 106 is inserted into the encaser liner such that the inner side of the encaser is not in direct contact with the therapeutic composition 106. The encaser liner may be made of material selected from paper, textile, non-woven fabrics, plastic fabrics, non-woven polypropylene fabrics, and any combination there of. The encaser liner may be opaque or may have any level of transparency, and may have any tint of color. The addition of the encaser liner provides a range of functions such as heat insulation, even heating, overheating spot prevention, moisture retaining, absorbency, resilience, stretch, softness, strength, cushioning, padding, filtering and sterility. Additionally, the encaser liner provides a medium support or a holding agent for any form of therapeutic composition 106 including, but not limited to, mud-based, clay-based, wax-based, liquid-based and gel-based compositions, such that the therapeutic composition 106 is attached, fixed, stick, adsorbed, absorbed to or by the encaser liner to reduce mobility within the encaser, and enables an ease assembly of the skin therapy systems 100 during manufacturing, packaging, and user application. In one embodiment, the encaser liner is made of paper sheet. In another embodiment, the encaser liner is made of non-woven polypropylene fabric. In one embodiment, a body part shaped encaser comprises an encaser liner and one therapeutic composition 106 contained in the encaser liner; wherein the encaser liner is made of non-woven poly propylene fabric.

(b) Temperature Indicators

A single-use body part shaped encaser may further comprise a means for visually indicating the temperature range of a therapeutic composition 106 during and after heating. This feature is provided to assist in preventing overheating of therapeutic composition 106 and to monitor the temperature of the skin therapy device during the therapy. For example, 126° F. is a recognized temperature safety limit in the industry. A therapeutic composition 106 with a temperature above 126° F. is not suitable for direct application on top of skin. The temperature indicator may be a coating, a strip, sticker, a label, a tape, or any other form that is applicable. The temperature indicator may be reversible or irreversible depending on the indications desired to be given. Single-use body part shaped encaser comprises at least one temperature indicator. In one embodiment, the temperature indicator is a thermochromatic indicator. In one embodiment, the temperature indicator comprises at least one thermochromatic coating structured and arranged to visibly indicate internal therapeutic composition temperature of a respective body part shaped encaser comprising therapeutic composition. In one embodiment, one or more thermochromatic indicator is located on the interior side of the encaser. In one embodiment, thermochromatic indicator may be applied as a thermochromatic patch, sticker to the exterior surface of the encaser. Thermochromatic indicator functions to visually indicate the approximate temperature of therapeutic composition such that the user is warned if the temperature is above or under a desired range of temperature. The visual indication may be through a change of color, or a showing of a number presenting a temperature, a level of temperature, a range of temperature, or other number or text that is meaningful to a skin therapy. Other temperature indicators may include pop-up notifiers, sound notifiers as known in the art.

As an exemplification, a single-use glove 102 in FIG. 2 comprises a thermochromatic indicator 118. The thermalchromatic indicator 118 may be positioned anywhere on the surface of the encaser, including on each finger-tip, at the thumb-tip, and at the palm area of single-use glove 102. Similarly, single-use boot 104 may also comprise thermochromatic indicator 118, positioned anywhere including at the ankle area and at the toe area of single-use boot 104. In one example, thermochromatic coating 110 and thermochromatic sticker 112 preferably change to at least one warning-temperature color, when therapeutic composition 106 exceeds at least one ideal temperature range. Upon reading this specification, those with ordinary skill in the art will now appreciate that, under appropriate circumstances, considering such issues as design preference, user preferences, marketing preferences, cost, structural requirements, available materials, technological advances, etc., other temperature arrangements such as, for example, greater or lesser temperatures, varying ranges of temperatures, more or fewer temperature indicators, etc., may suffice.

(c) Attach Means

Once a single-use body part shaped encaser comprising a therapeutic composition 106 is applied to the targeted skin area, an attach means is needed to attach and stabilize the encaser to the skin area for a period of therapy time. The attach means may be chosen from adhesive tape, straps, strings, elastic material, fabric tape, tubing, or other functional devices. The attach means may or may not be included in the skin therapy system. In one embodiment, a body shaped encaser comprises an attach means.

Figure 7:
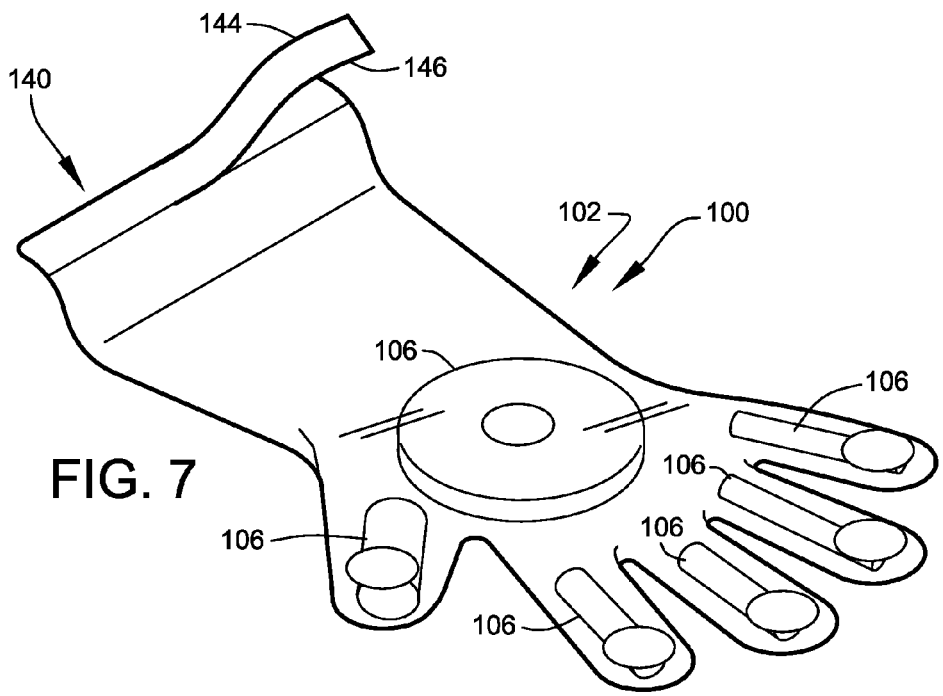
FIG. 7 shows a perspective view illustrating a hand glove of the wax therapy systems, according to the preferred embodiment of FIG. 1.

FIG. 7 shows a perspective view of an exemplary hand glove 102 of the skin therapy system 100, wherein the hand glove 102 comprises at least one aperture seal 144. In one embodiment, aperture seal 144 further comprises at least one strap 146, which includes at least one adhesive strip 148. In use, after a user inserts a hand, or alternately a foot, into single-use body part shaped encaser 120, strap 146 can be wrapped around and affixed to a wrist or an ankle using adhesive strip 148 to ensure attachment and stability of the skin therapy system 100 during therapy. Strap 146 and strip 148 may vary in width and length. In one embodiment, strap 146 has a length of about seven inches and a width of about one-half inch. In one embodiment, strap 146 is attached to single-use body shaped encaser 120 through at least one seam. Alternately, strap 146 is attached to single-use body shaped encaser 120 by heat welding or mechanical attachment means. In one embodiment, adhesive strip 148 comprises a length of from about one-half-inch to about four-inches.

(d) Other Additions

The skin therapy system 100 as disclosed herein may further comprise one or more external padding, outer pouch, coverlet, harness, heating or temperature maintaining element, stand alone user instruction, or instruction attached to the single use body part shaped encaser. The instruction may be in a print, a writing, a disk, or any other suitable medium. In one embodiment, one or more heating or temperature maintaining elements is attached to the exterior surface of the body part shaped encaser of the skin therapy system 100. In one embodiment, one or more heating or temperature maintaining elements is attached to the exterior surface of the body part shaped encaser of the skin therapy system 100.

II. Therapeutic Composition

The therapeutic composition 106 of the skin therapy system 100 may be solid, semi-solid or liquid under the room-temperature. In some embodiment, the therapeutic composition 106 is mud-based. In some embodiment, the therapeutic composition 106 is clay-based. In some embodiments the therapeutic composition 106 is wax-based, and the wax may be in a solid, semi-solid or liquid state. In some embodiments, therapeutic composition 106 does not comprise wax, and is mostly in a liquid state. The therapeutic composition 106 may be pre-packaged or packaged prior to the commencement of a therapy session such that it is enclosed in the body part shaped encaser of the skin therapy system 100 as disclosed herein. Upon application, the targeted skin area is in direct contact with the therapeutic composition 106. The formulation of the therapeutic composition 106 may vary depending on the skin condition to be treated, therapeutic purposes, or specific portions of a body part shaped encaser of the skin therapy system 100, for example, fingers versus palm, toes versus ankles.

1. Wax Based Therapeutic Composition

The therapeutic composition 106 of the skin therapy system 100 may be a wax-based composition. The wax may be selected from paraffin wax, soy wax, beeswax, palm wax. In one embodiment, the therapeutic composition 106 is paraffin based. Paraffin utilized in the present embodiments can soften, hydrate and protect the skin and may also be used as a treatment for some skin disorders. The paraffin may be selected from paraffin wax, liquid paraffin oil (also called mineral oil, nujol, adepsine oil, alboline, glymol, medicinal paraffin, or saxol), semi-solid paraffin (also called petroleum jelly, petrolatum, white petrolatum or soft paraffin), and any derivatives thereof. The paraffin wax based therapeutic composition 106 has a melting point temperature in the range between about 46° C. and about 68° C., between about 44° C. and about 60° C., between about 42° C. and about 55° C., between about 39° C. and about 50° C.

Figure 8:
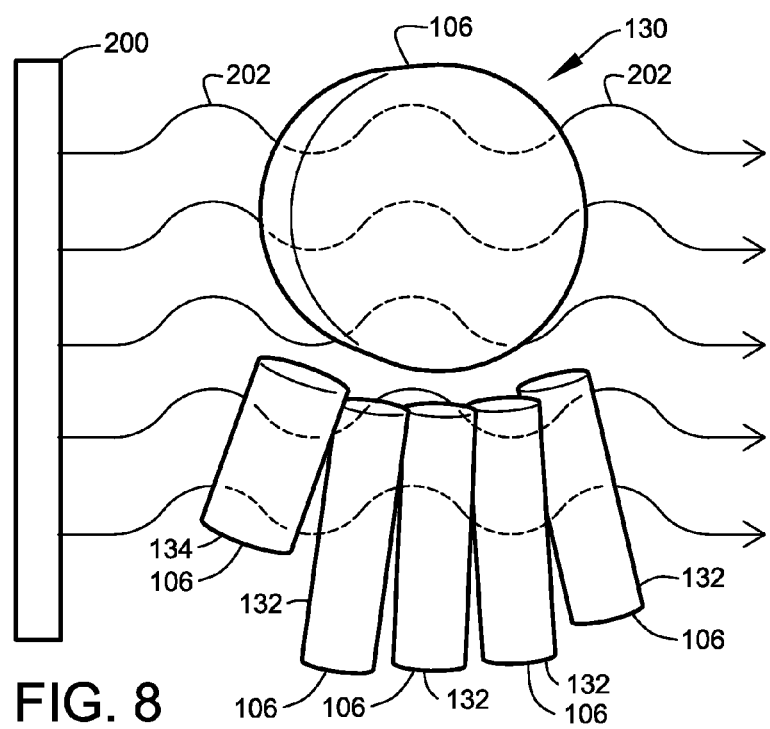
FIG. 8 shows a diagrammatic view illustrating heating of at least one therapeutic substance, according to the preferred embodiment of FIG. 1.

In a traditional commercial setting for skin therapy, the customary melt time for standard paraffin is approximately 10-15 minutes or longer in a standard non-commercial microwave (750-1000 watts) depending on the quantity being heated. Such a period of heating time is too long and thus not ideal. Further, as shown in FIG. 8, it was observed that uneven heating occurs in therapeutic composition 106 when the therapeutic composition 106 is enclosed in a body part shaped encaser such as a glove or a booty, when using microwave heating. This uneven heating causes the fingers and thumb in a glove to have a substantially higher temperature than the palm area when the same therapeutic composition 106 is used in all areas. Not to be bound by theory, it is believed that due to the dielectric heating effect of microwaves 202 from microwave producer 200, variations in volumes and surface areas of therapeutic composition 106 in various areas of single-use glove 102 cause variations in microwave absorption. In order to compensate for the variation in microwave absorption, and thus the particular amount of heat absorbed, between finger composition 132, thumb composition 134, and palm composition 130, the formulations of the therapeutic composition 106 were further modified such that the uniform melting of the therapeutic composition 106 in a body part shaped encaser to be achieved.

In order to reduce the melting time of a paraffin based therapeutic composition 106, various nut or seed oils including safflower oil, vitamin E oil, coconut oil, among other oils, were tested for their effects of paraffin wax melting time after being mixed with the paraffin wax. Theoretically, the use of oils helps to lower the initial viscosity of the paraffin composition and accelerates the melting process. However, not all tested oils can achieve that purpose. An ideal melting time for the therapeutic composition 106 of the skin therapy system 100 disclosed here in is between about 1 to 2 minutes depending on the heating sources.

During testing, many different types of oils, once mixed with the paraffin wax, made the melted paraffin wax runny and would not allow the wax to re-form or re-solidify. Some seed or nut oils don't even mix well with paraffin. In addition, re-solidification or gelification is preferred for easy application and removal of the skin therapy system 100 during and after the therapy. Surprisingly, the mixing of coconut oil with the paraffin is homogenized, and more important, at certain range of ratio the mixture allowed re-solidification or gelification of the paraffin-based therapeutic composition 106, when achieving a comparatively shortened melt time. Not to be bound by the theory, this preferred property for a therapeutic composition 106 is achieved probably because coconut oil comprises a more solid state in comparison to other oils at typical room temperatures (below about 80 degrees Fahrenheit). Shortened time of melting and re-solidification or gelification is desirable, in that it shortens the preparation time and enables the formation and shaping of the therapeutic composition 106 into a body part shape much easier and faster either during the therapy or before and after the therapeutic composition 106 is enclosed in an body part shaped encaser of the skin therapy system 100 as disclosed herein. In one embodiment, a paraffin based therapeutic composition 106 of the skin therapy system 100 as disclosed herein comprises paraffin and one or more nut oils including coconut oil. In one embodiment, a paraffin based therapeutic composition 106 of the skin therapy system 100 as disclosed herein comprises paraffin and coconut oil.

Continued experimentation with formulations by adding and changing combinations paraffin and coconut oil revealed, surprisingly, that the best combination for the therapeutic composition to hold up on the skin with a preferred body part shaped, shell-like effect while still melting in under 2 minutes is to mix the paraffin with coconut oil at a ratio of from about 1:3 to about 3:1, by weight of the therapeutic composition 106. Some variations are utilized in such a mixture as described herein to assist even-melting in a given glove or boot or other body part shaped encaser with or without an encaser liner as disclosed herein. In one embodiment, preferably, the therapeutic composition 106 of the skin therapy system 100 comprises paraffin at a concentration in a range of about 25 wt % to about 75 wt % and coconut oil at a concentration in a range of about 25 wt % to about 75 wt %. More preferably, the therapeutic composition 106 of the skin therapy system 100 comprises from about 30 wt % to about 60 wt % of coconut oil and from about 40 wt % to about 70 wt % of paraffin. In one embodiment, the therapeutic composition 106 of the skin therapy system 100 comprises from about 35 wt % to about 55 wt % of coconut oil and from about 45 wt % to about 65 wt % of paraffin. In one embodiment, the therapeutic composition 106 of the skin therapy system 100 comprises from about 35 wt % to about 55 wt % of coconut oil and from about 45 wt % to about 65 wt % of paraffin. In one embodiment, the therapeutic composition 106 of the skin therapy system 100 comprises about 50 wt % of coconut oil and about 50 wt % of paraffin.

To achieve a simultaneously complete melting of all compositions in a body part shaped encaser, other alterations to change the latent heat of fusion of composition in fingers, toes, palm and anchor of the encaser were tested, for example by using two or more different therapeutic compositions 106 at different portions of a body part shaped encaser. Without being bound by theory, more heat absorption is required in areas previously overheated is required and less heat absorption is required in areas previously under-heated to effect a change in the state of matter from solid to liquid. As such, having various latent heats, each therapeutic composition 106 preferably melts and achieves a temperature within the ideal temperature range after the same amount of time exposed to a heating source such as microwave. In one embodiment, the palm composition for a hand shaped encaser comprises at least about 25 wt % to about 75 wt % of paraffin and 25 wt % to about 75 wt % of coconut oil; and the finger composition and thumb composition for a hand shaped encaser comprise at least 50 wt % to 70 wt % of paraffin and at least about 30 wt % to about 50 wt % of coconut oil.

Therapeutic composition 106 as disclosed herein may further comprise at least one essential oil. For medical purposes, from about six to about twelve drops of medical grade essential oils may be added to the therapeutic composition 106. A drop of essential oils, as defined herein using the AFNOR-ISO standard for quantifying essential oils, is about $\frac{1}{20}^{th}$ of one milliliter when utilizing the standard of 20 drops per milliliter of essential oil (for example, see UTL: anandaapothecary.com/measuring-essential-oils.html). When the standard for a specific essential oil is different due to viscosity, a single-drop volume may be adjusted accordingly. In one embodiment, the essential oils are added and mixed into the therapeutic composition 106 before the therapeutic composition 106 is enclosed in a body part shaped encaser of the skin therapy system 100. In one embodiment, the essential oils are added into the therapeutic composition 106 prepackaged in a body part shaped encaser of the skin therapy system 100 upon applying the same to a targeted skin area, such that different essential oils may be used for a specific condition of a specific individual under the therapy. Essential oils and aromatic oils of the therapeutic composition 106 may be selected from peppermint oil, cinnamon leaf oil, lemongrass oil, clove oil, castor oil, orange oil, *eucalyptus* oil, tea tree oil, wintergreen oil, patchouli oil, lavender, bergamot, sandalwood, chamomile, aldehyde C16, α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol, eugenol, iso-eugenol, galaxolide, geraniol, guaiacol, ionone, menthol, methyl salicylate, methyl anthranilate, methyl ionone, a-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and combinations thereof. Other essential oils that are applicable to the therapeutic composition of the skin therapy systems may be found at the UTL: organicfacts.net/organic-oils/natural-essential-oils/list-of-essential-oils.html and other sources.

In one embodiment, a preferred essential oil mixture for pain relieving comprise peppermint oil, cinnamon leaf oil, clary sage, orange oil. In one embodiment, a preferred essential oil mixture for anti-fungal and anti-bacterial effects comprises tea tree oil, clove oil, lemon oil, *eucalyptus* oil and patchouli oil. In one embodiment, a preferred essential oil mixture for relaxation comprises lavender, bergamot, sandalwood and chamomile. Additionally, aromatherapy oils may also be utilized to add further therapeutic effects. In one embodiment, the therapeutic composition 106 comprising paraffin, coconut oil, may further comprise at least one aromatic oil.

The paraffin based therapeutic composition 106 may further comprise optional additives including, but not limited to fragrances, colors, emollients, anti-oxidants, known in the art. The antioxidant used in the therapeutic composition 106 should not cause irritation to the skin when the therapeutic composition is applied. In addition, the antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), *eucalyptus* extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof. One skilled in the art will appreciate that the antioxidants incorporated into the composition (including those listed herein) encompass all potential salt and ester forms of the antioxidants in addition to the pure forms of the compound. Preferably, the antioxidant comprises a vitamin E compound such as tocopherol acetate, tocopherol linoleate, tocopherol nicotinate, tocopherol succinate, ascorbyl tocopherol phosphate, dioleyl tocopherol methylsilanol, tocophersolan, and tocopherol linoleate/oleate. In one embodiment, included in the vitamin E oil are traces of safflower oil, and other oils. In another embodiment, the vitamin E formula further comprises the largest amount of sunflower seed oil followed by safflower seed oil, tocopheryl acetate, rice bran oil, almond oil, apricot oil, wheat germ oil and lecithin. In one embodiment of the therapeutic composition 106 comprising paraffin at a concentration in a range of about 25 wt % to about 75 wt % and coconut oil at a concentration in a range of about 25 wt % to about 75 wt %, the therapeutic composition 106 further comprises from about 2 wt % to 7 wt % of a mixture of antioxidant.

2. Liquid-Based Therapeutic Composition

The therapeutic composition 106 of the skin therapy system 100 as disclosed herein may be a liquid-based composition, such that a solid to liquid, then back to solid phase changes are not involved. In some embodiments, a pre-heating or pre-cooling step before application may be required. In some other embodiments, a pre-heating or pre-cooling step before application may not be required. In one embodiment, the liquid based composition comprises an active therapeutic component 106 selected from alpha hydroxy acid including lactic acid, glycolic acid; and/or beta hydroxy acid including salicylic acid, and any combination thereof. The liquid based composition comprising alpha hydroxy acid including lactic acid, glycolic acid; and/or beta hydroxy acid including salicylic acid may further comprise essential oils, fragrances, colors, emollients, anti-oxidants, and other additives including absorbent, adsorbent, pH controller, substances for rehydration known in the art. In one embodiment, a liquid based therapeutic composition 106 for the skin therapy system 100 comprises lactic acid, glycolic acid, salicylic acid, lemon oil, polyquaternium-10, PEG-40 hydrogenated castor oil, sodium hydroxide, and one or more antioxidant including vitamin E. Various suitable essential oils and anti-oxidants for a liquid-based composition are described above in detail.

III. Method of Using the Skin Therapy Systems for Skin Treatment

This invention also provides a method relating to providing skin treatment utilizing a therapeutic composition 106 contained in a body part shaped encaser amenable to various heating elements to provide liquefaction before use without burning the skin. The method of using the skin therapy system 100 as disclosed herein for skin treatment generally comprises the steps of heating the encaser containing a therapeutic composition 100 using one or more heating elements, applying the unsealed encaser to targeted skin area by attaching the encaser to a body part, and removing the encaser from the targeted skin area at the end of the therapy.

Some paraffin based therapeutic composition 106 need to be heated to melt prior to application. Paraffin wax typically has a melting point temperature in the range between about 46° C. (114.8° F.) and about 68° C. (154.4° F.). Petroleum jelly based therapeutic compositions 106 have a melting-point usually within a few degrees of human body temperature, which is approximately 37° C. (98.6° F.). Liquid paraffin-based therapeutic composition 106 and other liquid based composition may need to be pre-heated to body temperature for the comfortable feel to the skin upon application. Depending on the storage condition, room temperature, and specific therapeutic temperature requirement, the therapeutic composition 106 enclosed in a body part shaped encaser of the skin therapy system 100 as disclosed herein may require a heating process by a heating element. Suitable heat element may be selected from microwave oven, stove, hot towel cabinet, heating coils, heating pad, heater, heating lamp, warmer, radiator, boiler, steamer, and any other device or equipment known in the art. In one embodiment, the heating element is portable. As disclosed herein, in some embodiments, the heating element is comprised in the skin therapy system 100. The heating temperature may be provided by a heating element included the skin therapy system 100, and the temperature of the therapeutic composition 106 may be indicated by touching or temperature indicator attached to the body part shaped encaser of the skin therapy system 100. Preferably, with a heating time of a therapeutic composition 106 between 1-5 minutes, or preferably 1-2 minutes, the melting temperature of a therapeutic composition 106 ranges from about 45° C. (113° F.) to about 55° C. (131° F.). More preferably, with a heating time of a therapeutic composition 106 between 1-2 minutes, the melting temperature of a therapeutic composition 106 ranges from about 48° C. (119° F.) to about 51° C. (124° F.). In one embodiment, the therapeutic composition 106 comprising paraffin at a concentration of about 25-75 wt %, by weight of the composition, and coconut oil at a concentration of about 25-75 wt % by weight of the composition has a melting temperature between about 48° C. to about 51° C., and an even melting of the composition takes place in about 1-5 minutes.

After a predetermined temperature range of a therapeutic composition 106 of the skin therapy system 100 is reached, the sealed encaser containing the therapeutic composition 106 is opened by cutting, unzipping or tearing the enclosure of the encaser. Inserting the body part into the encaser such that the targeted skin area is in direct contact with the therapeutic composition 106, through touching, dipping, or being covered by the therapeutic composition 106. The encaser is then attached to the body part using adhesive tape, strap, string elastic band, or tubing for stabilization during the therapy. The application may last for 10 minutes, 20 minutes, 30 minutes, 60 minutes, 120 minutes or longer, or any range of duration in between. When the therapy ends at a time point, the encaser is released from the body part by removing the attachment means and thus the encaser comprising the therapeutic composition 106.

Figure 9:
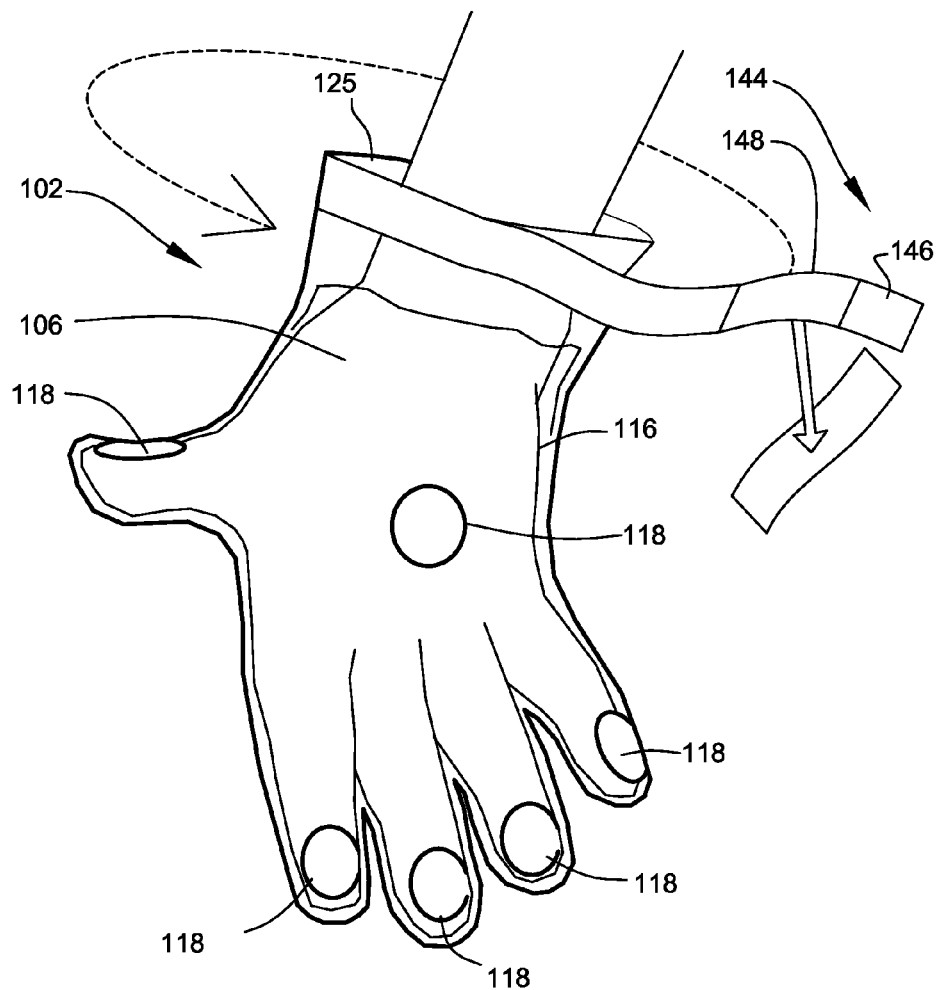
FIG. 9 shows a perspective view illustrating use of a hand glove of the wax therapy systems, according to the preferred embodiment of FIG. 1.
Figure 10:
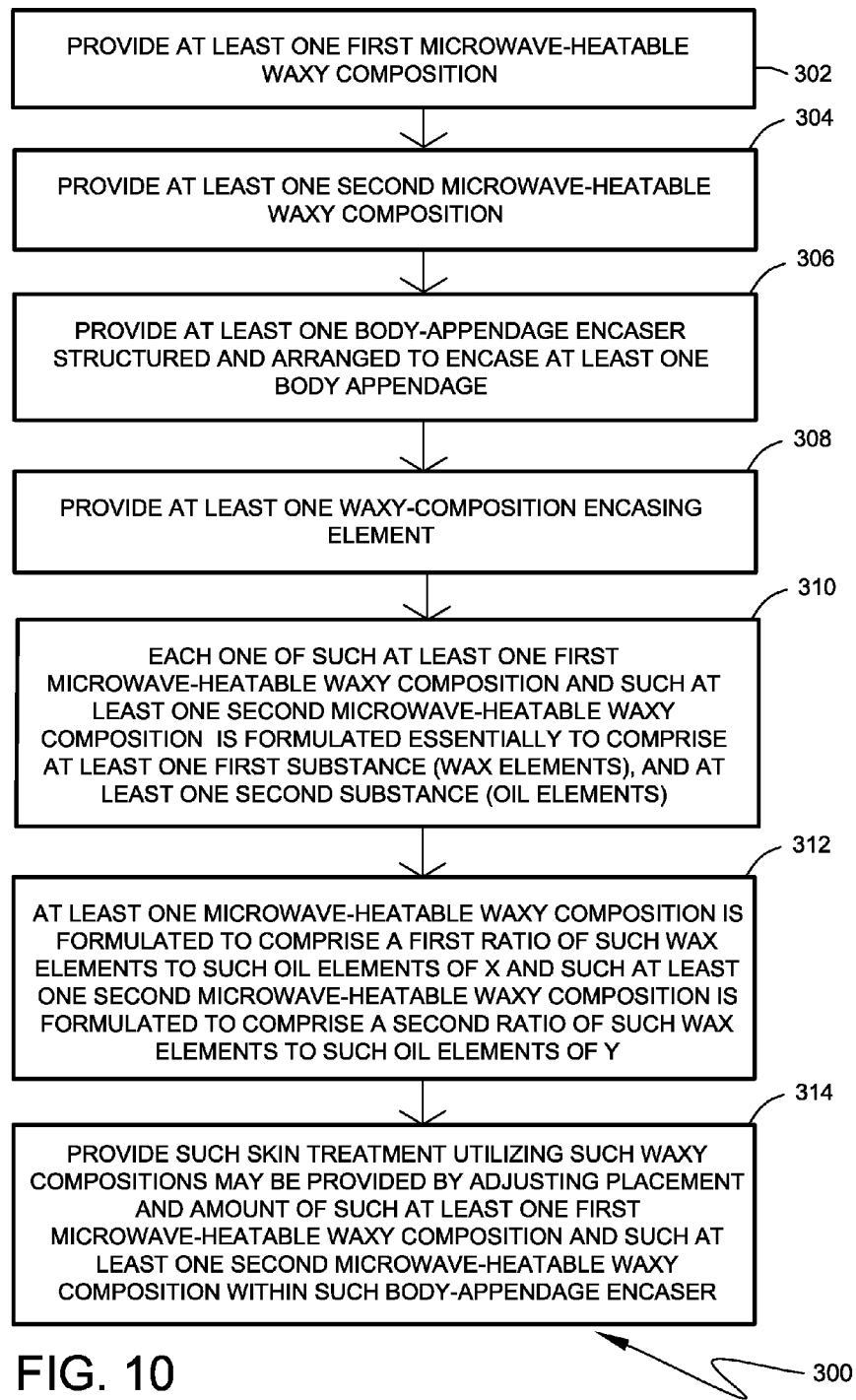
FIG. 10 shows a flow diagram illustrating preferred steps of a method relating to providing skin treatment utilizing waxy compositions amenable to microwave heating to provide liquefaction before use without skin burning, according to the preferred method of the present invention.

The method of using the skin therapy systems 100 as disclosed herein for skin treatment may further comprise assembling the body part shaped encaser. Referring to the flow diagram of FIG. 9 as an example, in which a microwave oven is used as a heating element in method 300 comprises the following preferred steps. In initial step 302 of method 300 a first wax-based composition is formulated to be heatable by a microwave energy producer. Next, as indicated in step 304 a second microwave-heatable wax-based composition is formulated to be heatable by a microwave energy producer. Next, as indicated in step 306 at least one body part shaped encaser structured and arranged to encase a body part of a human body is provided. As indicated in Step 308 one or more microwave-heatable wax-based composition is encased by spreading the composing into a thin layer in the encaser. As indicated in Step 310 each one of such microwave-heatable wax-based composition is formulated to comprise at least one first substance, and at least one second substance; wherein such first substance comprises wax elements; wherein the second substance comprises an oil element. Step 312 indicates that a first microwave-heatable wax-based composition is formulated to comprise a first ratio X of wax element to the oil elements, and a second microwave-heatable wax-based composition is formulated to comprise a second ratio Y of wax element to the oil elements. Preferably, the latent heat of fusion of the resulting first microwave-heatable wax-based composition is substantially different from the latent heat of fusion of the second microwave-heatable waxy composition. Finally, as indicated in Step 314, a skin treatment utilizing such wax-based compositions amenable to microwave heating to provide liquefaction before use without skin burning may be provided by adjusting placement and amount of a first microwave-heatable wax-based composition and a second microwave-heatable wax-based composition within a body part shaped encaser to equalize the melting of the wax-based composition to assist prevention of injuring skin tissues of the body part to be treated.

Figure 6B:
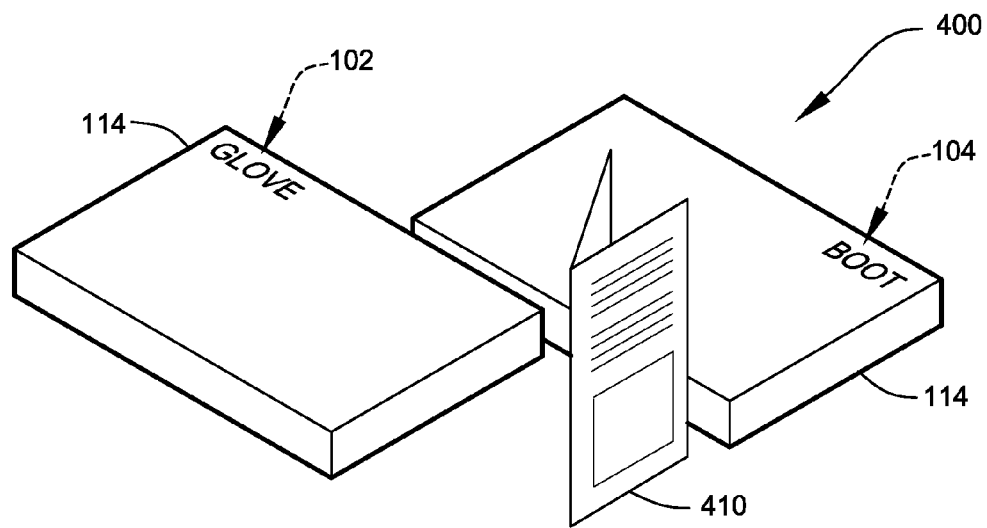
FIG. 6B shows a perspective view of a preferred pre-packaged kit/apparatus according to the preferred embodiment of the present invention.

As an additional example, FIG. 6B shows an illustrative set of instructions for using a pre-packaged kit/apparatus according to an embodiment of the present invention. In one embodiment of a method of use, single-use wax-based therapy device 120 may be provided as a prepackaged Kit 400 (See FIG. 4A, FIG. 4B and FIG. 6A and FIG. 6B) comprising a microwavable sealing box 114 comprising at least one single-use glove 102 or single-use boot 104 comprising one or more therapeutic composition and at least one set of instructions 410.

It should be understood that the invention is not limited to the particular embodiments described herein, but that various changes and modifications may be made without departing from the spirit and scope of this novel concept as defined by the following claims. Further, many other advantages of applicant's invention will be apparent to those skilled in the art from the above descriptions and the below claims.

I claim:

1. A skin therapy system for skin conditioning or treatment of a body part, the system comprising:
   (a) a body part shaped encaser configured to fit a body part targeted for skin treatment;
   (b) one or more predetermined amount of therapeutic compositions enclosed in the body part shaped encaser, wherein the therapeutic composition comprises about 25 wt % to about 75 wt % paraffin, about 25 wt % to about 75 wt % coconut oil, and about 2 wt % to 7 wt % of a mixture of antioxidants comprising tocopheryl acetate, by weight of the composition; and
   (c) a sealing means that seals the body part shaped encaser enclosing the one or more therapeutic compositions, wherein the sealing means is attached to the body part shaped encaser or is detached from the body part shaped encaser.

2. The skin therapy system of claim 1, wherein the mixture of antioxidants further comprises one or more additional ingredients selected from the group consisting of sunflower seed oil, safflower oil, rice bran oil, almond oil, apricot oil, wheat germ oil, lecithin, and any combination thereof.

3. The skin therapy system of claim 1, wherein the paraffin in the one or more therapeutic compositions is selected from the group consisting of paraffin wax, liquid paraffin oil, petroleum jelly, and any combination thereof.

4. The skin therapy system of claim 1, wherein the one or more therapeutic compositions enclosed in the body part shaped encaser liquefies in between about 1 and about 5 minutes at a temperature ranging from about 113° F. to about 131° F.

5. The skin therapy system of claim 1, wherein the sealing means is a vacuum seal to keep air out of the body part shaped encaser enclosing the one or more therapeutic compositions.

6. The skin therapy system of claim 1, the system further comprises one or more temperature indicators, wherein the one or more temperature indicators are attached to an exterior surface of the body part shaped encaser.

7. The skin therapy system of claim 6, wherein the one or more temperature indicators are a thermochromatic indicator in a form selected from the group consisting of a coating, a strip, a sticker, a label, a patch, and a tape.

8. The skin therapy system of claim 7, wherein the thermochromatic indicator indicating a temperature ranging from about 113° F. to about 131° F.

9. The skin therapy system of claim 1, further comprises one or more accessories selected from the group consisting of a temperature indicator, an attachment means, an external padding, an outer pouch, a coverlet, a harness, a heating or temperature maintaining element, and any combination thereof.

10. The skin therapy system of claim 1, wherein the body part shaped encaser is configured in a form selected from the group consisting of a glove, a mitten, a muff, a fingerstall, a sock, a slipper, a shoe, a booty, a bonnet, a skullcap, a facial mask, and any other structure adaptable for covering an area of skin of a body part to be treated.

11. The skin therapy system of claim 1, wherein the body part shaped encaser is made from material selected from the group consisting of carbon-fiber, polyethylene, metal foil, and any combination thereof.

12. The skin therapy system of claim 1, wherein the body part shaped encaser has a standard size and dimension.

13. The skin therapy system of claim 1, wherein the body part shaped encaser further comprises an encaser liner of similar size, dimension and shape to the encaser, and wherein the encaser liner is inserted in the body part shaped encaser and the one or more therapeutic compositions is enclosed in the encaser liner.

14. The skin therapy system of claim 13, wherein the encaser liner is made from material selected from the group consisting of paper, textile, non-woven fabrics, plastic fabrics, non-woven polypropylene fabrics, and any combination thereof.

15. The skin therapy system of claim 1, wherein the one or more therapeutic compositions further comprise one or more additional ingredient selected from the group consisting of essential oils, anti-oxidants, fragrances, colors, emollients and any combination thereof.

16. A method of using a skin therapy system for skin conditioning or treatment of a body part, wherein the method comprising:
   (a) pre-heating a body part shaped encaser of the skin therapy system to liquefy one or more therapeutic compositions enclosed in the body part shaped encaser, wherein the therapeutic composition comprises about 25 wt % to about 75 wt % paraffin, about 25 wt % to about 75 wt % coconut oil, and about 2 wt % to 7 wt % of a mixture of antioxidants comprising tocopheryl acetate, by weight of the composition;
   (b) removing a sealing means of the body part shaped encaser enclosing the one or more therapeutic compositions;
   (c) inserting a body part targeted for skin treatment into the encaser to put the skin in direct contact with the one or more therapeutic compositions;
   (d) attaching the body part shaped encaser enclosing the one or more therapeutic compositions to the body part using an attach means; and
   (e) detaching the body part shaped encaser enclosing the one or more therapeutic compositions from the body part after a predetermined amount of time.

17. The method of claim 16, wherein the mixture of antioxidants further comprises one or more additional ingredients selected from the group consisting of sunflower seed oil, safflower oil, rice bran oil, almond oil, apricot oil, wheat germ oil, lecithin, and any combination thereof.

18. The method of claim 16, wherein the paraffin in the one or more therapeutic compositions is selected from the group consisting of paraffin wax, liquid paraffin oil, petroleum jelly, and any combination thereof.

19. The method of claim 16, wherein the one or more therapeutic compositions further comprise one or more additional ingredient selected from essential oils, anti-oxidants, fragrances, colors, emollients and any combination thereof.

20. A skin therapy system for skin conditioning or treatment of a body part, the system comprising:
   (a) a body part shaped encaser configured to fit a body part targeted for skin treatment;
   (b) one or more predetermined amount of therapeutic compositions enclosed in the body part shaped encaser, wherein the therapeutic composition comprises about 25 wt % to about 75 wt % paraffin, about 25 wt % to about 75 wt % coconut oil, and about 2 wt % to 7 wt % of a mixture of antioxidants comprising tocopheryl acetate, by weight of the composition;
   (c) a sealing means that seals the body part shaped encaser enclosing the one or more therapeutic compositions, wherein the sealing means is attached to the body part shaped encaser or is detached from the body part shaped encase, and (d) a thermochromatic indicator indicating a temperature ranging from about 113° F. to about 131° F.

* * * * *